United States Patent [19]

Pickett et al.

[11] Patent Number: 5,679,820
[45] Date of Patent: Oct. 21, 1997

[54] SILYLATED ULTRAVIOLET LIGHT ABSORBERS HAVING RESISTANCE TO HUMIDITY

[75] Inventors: James Edward Pickett, Schenectady; Gregory Ronald Gillette, Clifton Park, both of N.Y.

[73] Assignee: General Electric Company, Schenectady, N.Y.

[21] Appl. No.: 766,655

[22] Filed: Dec. 16, 1996

[51] Int. Cl.⁶ ............................. C07F 7/08; C07F 7/18
[52] U.S. Cl. ............... 556/436; 106/287.14; 428/412; 428/447
[58] Field of Search ............... 556/436; 106/287.14; 428/412, 447

[56] References Cited

U.S. PATENT DOCUMENTS

| | | |
|---|---|---|
| 5,214,085 | 5/1993 | Patel et al. |
| 5,391,795 | 2/1995 | Pickett. |
| 5,606,089 | 2/1997 | Tamura et al. ........................... 556/436 |

Primary Examiner—Paul F. Shaver
Attorney, Agent, or Firm—Noreen C. Johnson; William H. Pittman

[57] ABSTRACT

The instant invention is directed to novel silylated agents having the formula

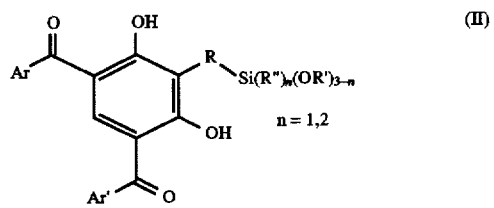

where Ar and Ar' are independently substituted or unsubstituted aromatic rings, R is a branched or unbranched chain of 1 to 6 carbons, R' and R" are independently C1 to C12 alkyl or mixtures of C1 to C12 alkyl, and n is 1 or 2. The novel dibenzoylresorcinol silylated agents are capable of absorbing ultraviolet light.

21 Claims, No Drawings

SILYLATED ULTRAVIOLET LIGHT ABSORBERS HAVING RESISTANCE TO HUMIDITY

FIELD OF THE INVENTION

This invention relates to novel silylated compositions capable of absorbing ultraviolet light and methods of making the compositions. Particularly, the compositions are dibenzoyl alkoxysilylalkyl resorcinols having less than three alkoxy groups on the silicon which are photostable and compatible in silicone hardcoat matrices.

BACKGROUND OF THE INVENTION

Thermoplastic substrates such as polycarbonates are generally characterized by many advantageous properties which include clarity, high ductility, high heat deflection temperature, as well as dimensional stability. Many of these materials are transparent and are conventionally employed as replacements for glass in commercial applications.

While thermoplastic resins possess the above-described advantageous properties, they often display low abrasion and chemical solvent resistances, and like many other organic polymeric materials, they are susceptible to degradation by ultraviolet light. This results in unfavorable characteristics including yellowing and erosion of the substrate surface.

Recently, it is of increasing interest to prepare resinous thermoplastic substrates, such as polycarbonates, that are resistant to abrasion and photodegradation. This is often accomplished by treating the substrate surface with a silicone hardcoat material, whereby the coating material typically contains ultraviolet light absorbing agents, such as benzotriazoles and benzophenones, and hindered amine light stabilizers.

It is often discovered, however, that the ultraviolet light absorbing compounds (herein also referred to as UV absorbers), themselves, decompose upon exposure to ultraviolet light. Prolonged exposure to sunlight, moisture and thermal cycling conditions can cause yellowing, delamination and formation of microcracks in the coating material, decreasing transparency. This leads to a degradation of the favorable properties of the thermoplastic substrate which the UV absorbers are originally employed to protect. Thus, there is an ongoing need to seek new, efficient UV absorbing compounds for use in abrasion resistant, highly weatherable coatings.

In commonly owned and assigned U.S. Pat. No. 5,391,795, incorporated herein by reference, there is disclosed a UV absorber based on 4,6-dibenzoylresorcinol bearing a trialkoxysilyl group on a short alkyl chain as shown by the formula

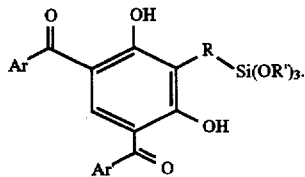

The above-mentioned UV absorber has excellent photostability due to the chromophore in the silicone hardcoat matrix. It was thought that the trialkoxygroup was essential for good compatibility and abrasion resistance. It has since become apparent that the trialkoxysilane derivatives suffer from poor hydrolytic stability. This is observed when the solid silylated UV absorber is allowed to be in contact with moist air for periods as little as a 2 to 3 days to several weeks. A solid crust forms on the silylated UV absorber which does not dissolve in the silicone hardcoat coating composition. While the insoluble material can be filtered off, some of the UV absorber is lost. Thus, there is also a need to develop derivatives based on 4,6-dibenzoylresorcinol which would have improved shelf stability while still making coatings with good abrasion resistance, UV absorbance, and excellent weatherability.

SUMMARY OF THE INVENTION

The instantly claimed invention satisfies these needs by providing novel dibenzoylresorcinol silylated agents capable of absorbing ultraviolet light. The silylated agents are 4,6-dibenzoyl-2-(dialkoxysilylalkyl) resorcinols or 4,6-dibenzoyl-2-(monoalkoxysilylalkyl) resorcinols which display photostability, compatibility in silicone hardcoat and UV curable acrylic matrices, and improved hydrolytic stability.

In a first aspect, the instant invention is directed to novel silylated agents having the formula

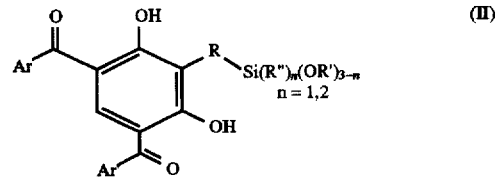

where Ar and Ar' are independently substituted or unsubstituted aromatic rings, R is a branched or unbranched chain of carbons, R' and R" are independently C1 to C12 alkyl or mixtures of C1 to C12 alkyl, and n is 1, 2, or 3. A preferred amount of carbons for R is 1 to 6 carbons. Often, the silylated agent is a 4,6 dibenzoyl-2-(alkoxysilylalkyl) resorcinol and preferably, 4,6-dibenzoyl-2-(3-alkoxysilylpropyl) resorcinol.

In a second aspect of the instant invention, the novel silylated agents described above are incorporated into thermally cured silicon compound-containing compositions. Said compositions comprising the silylated agents are coating compositions defined as silicone hardcoats or topcoats.

In a third aspect of the invention, the novel silylated agents described above are incorporated into UV-curable acrylic coating compositions. The coating compositions are defined as coatings comprising the silylated agents and a substantially transparent matrix composition. Generally, the matrix material contains acrylics, urethanes, melamines, or mixtures thereof. Copending and commonly assigned U.S. patent application Ser. No. 08/699,254, filed Aug. 15, 1996, herein incorporated be reference, also describes coating compositions.

In a fourth aspect of the instant invention, the above described silicone hardcoats or UV-curable coatings are applied to the surface of a solid substrate thus producing a coated solid substrate having improved resistances to abrasion and ultraviolet light. Such coated solid substrates are often referred to as weatherable substrates. Further, there are no limitations with respect to the thickness of the coatings applied to said solid substrates. They are, however, often about 0.5 to about 50 μm thick and preferably about 3 to about 15 μm thick. In the instant invention, the solid substrates that may be employed often include polymer substrates such as acrylic polymers including poly (methyl methacrylate), polyesters such as poly (ethylene terephthalate) and poly(butylene terephthalate), polyamides, polyimides, acrylonitrile-styrene copolymers, styrene-acrylonitrile-butadiene copolymers, polyvinyl chloride, polystyrene, blends of polystyrene and polyphenylene ethers, butyrates, polyethylene and the like. Thermoplastic substrates can be with or without pigments. Moreover, said solid substrates may also include metal substrates, painted surfaces, glass, ceramics and textiles. However, the coating compositions of the instant invention are preferably employed to coat polycarbonates.

Those skilled in the art will gain a further and better understanding of the present invention from the detailed description set forth below, considered in conjunction with the examples and chemical drawings accompanying and forming a part of the specification.

DETAILED DESCRIPTION OF THE INVENTION

It is discovered that dibenzoylresorcinol derivatives based on formula II can be prepared that have fewer than three alkoxy groups on the silicon yet still have excellent compatiblity in silicone hardcoat resins and surprisingly excellent abrasion resistance upon cure. In addition, derivatives with only one or two alkoxy groups have improved compatibility after exposure to moist air indicating better shelf stability of the materials.

In Formula II,

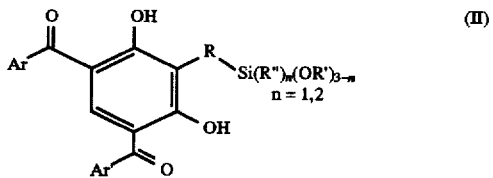

Ar and Ar' are independently substituted or unsubstituted aromatic rings, R is a branched or unbranched chain carbons, R' and R" are independently C1 to C12 alkyl or mixtures of C1 to C12 alkyl, and n is 1, 2, or 3. The preferred number of carbons for R is 1 to 6. The derivative with n=0 is the prior-art compound. The derivative with n=3 can be prepared, but its initial solubility may be limited in the coatings. Certain silyl derivatives are conveniently prepared by the hydrosilylation of the appropriate allyl or substituted allyl 4,6-dibenzoylresorcinol as shown in the Example 3 of the above-mentioned U.S. Pat. No. 5,391,795.

Preparation of the novel silylated agents, 4,6-dibenzoyl-2-(di or monoalkoxysilylalkyl) resorcinols employed in the instant invention is achieved, for instance, by first mixing a benzoyl halide and an aluminum halide in an organic solvent with a dialkoxybenzene to produce a 4,6-dibenzoylresorcinol. The 4,6-dibenzoylresorcinol is subsequently subjected to a quaternary ammonium salt and an allyl halide under basic conditions to produce a 2-allyl-4,6-dibenzoylresorcinol. The 2-allyl 4,6-dibenzoylresorcinol is contacted with a alkoxyhydrosilane in the presence of a hydrosilylation catalyst in order to produce the desired 4,6-dibenzoyl-2-(di or mono-alkoxysilylalkyl)resorcinol.

The preparation of the novel silylated agents of the instant invention is further illustrated by the following examples. Molecular structures of all products in the examples may be confirmed by proton and carbon-13 nuclear magnetic resonance spectroscopy.

EXAMPLES

Example 1

Preparation of Silylated UV Absorbers

2-Allyl-4,6-dibenzoylresorcinol (10.75grams, 30 mmol) was suspended in 40 milliliters of toluene. To this was added 2 drops of Karstedt's catalyst (complex of platinum in 1,3-divinyl-tetramethyldisiloxane) and the temperature was brought to 65° C. whereupon 35 mmol of the appropriate silane (shown in Table 1) was added. The temperature was held at about 65° to 85° C. for about 1 to 2 hours after which the reaction mixture was cooled, filtered, and evaporated to give amber oils which solidified upon cooling. The NMR spectra of the products were fully consistent with the expected structure. The yields are shown in Table 1. The products are Formula II where Ar and Ar' are phenyl, R is $CH_2CH_2CH_2$, R' is ethyl and R" is methyl.

TABLE 1

Yield of silylated dibenzoylresorcinol of formula II

| Entry # | Hydrosilane | R | R' | R | n | Yield |
|---|---|---|---|---|---|---|
| 1 | $HSi(OEt)_3$ | $CH_2CH_2CH_2$ | Et | — | 0 | 94% |
| 2 | $HSiCH_3(OEt)_2$ | $CH_2CH_2CH_2$ | Et | Me | 1 | 94% |
| 3 | $HSi(CH_3)_2OEt$ | $CH_2CH_2CH_2$ | Et | Me | 2 | 98 |
| 4 | $HSi(Et)_3$ | $CH_2CH_2CH_2$ | — | Et | 3 | 72% |

Example 2

Testing for Resistance to Humidity 1.0 gram samples of silylated dibenzoylresorcinol (DBR) derivatives 1 through 3 of Table 1 were ground to course powders and placed in aluminum pans above a dish of water in a dessicator to simulate extended exposure to moist air. After 24 days of exposure at room temperature, 0.50 gram portions of each was added to 20 gram samples of a silicone hardcoat resin (GE Silicones AS4004, 25% resin solids) and stirred overnight at room temperature. The resins were then filtered on 10–20 micron fritted glass funnels to measure the amount of insoluble material. The residues were dried to constant weight in a vacuum oven at about 140° C.

TABLE 2

Insolubles in coating resins prepared from "aged" UV absorbers.

| Entry # | silated DBR from Table 1 | Weight of insolubles (grams) | Percent insoluble |
|---|---|---|---|
| 1 | 1 | 0.241 | 48% |
| 2 | 2 | 0.001 | 0.2% |
| 3 | 3 | 0.009 | 1.8% |

Hardcoat formulations prepared with fresh silylated derivatives 1, 2 and 3 had only trace amounts of insolubles while derivative #4 was essentially insoluble in the coating solution. It can be seen that derivatives 2 and 3 had much improved resistance to the formation of insoluble residues compared with prior-art derivative 1.

Example 3

Coated Polycarbonate Panels

Coating resins were prepared as in Example 2 using fresh silylated derivatives 1, 2, and 3. These were filtered (removing only traces of insoluble materials). Lexan®, a registered trademark of General Electric Company, polycarbonate panels (4"×12"×⅛") were washed with isopropyl alcohol, dried, and primed by flowcoating with an aqueous acrylic emulsion primer. The primed panels were baked at about 128° C. in an air oven for about 60 minutes. The cooled panels were then flow coated with the coating resins, air dried for about 30 minutes, and baked at about 128° C. for about 60 minutes. The resulting coatings were substantially defect-free and optically clear. The center 4 inches of the panels were subjected to the Taber abrasion test (ASTM D1044-94) using CS-10F wheels for 500 cycles under 500 gram load. The results shown on Table 3 indicate substantially equivalent abrasion resistance within the error limits of the test. This is surprising in view of the commonly-held belief that use of di or mono-alkoxysilanes would lead to significantly decreased abrasion resistance.

TABLE 3

Abrasion resistance of hardcoated polycarbonate panels

| Entry # | DBR-silane from Table 1 | % Haze after Taber test |
|---|---|---|
| 1 | 1 | 10 |
| 2 | 2 | 12 |
| 3 | 3 | 11 |

Example 4

UV-curable Coatings

Coating formulations were prepared as shown below in Table 4.

TABLE 4

Coating compositions (parts by weight)

| | Component | | | |
|---|---|---|---|---|
| | A | B | C | D |
| Polyurethane hexacrylate (Ebecryl ® 1260) | 8 | 8 | 8 | 8 |
| FCS100 (GE Silicones acrylated colloidal silica) | 2 | 2 | 2 | 2 |
| Tinuvin ® 123 (Ciba Geigy) | 0.1 | 0.1 | 0.1 | 0.1 |
| Surfactant | 0.015 | 0.015 | 0.015 | 0.015 |
| 2,4,6-trimethylbenzoyl diphenyl phosphine oxide (initiator) | 0.3 | 0.3 | 0.3 | 0.3 |
| Isopropyl alcohol/propylene glycol monomethyl ether (1:1) | 20 | 20 | 20 | 20 |
| Aged DBR-silane 1 (Table 1) | 0.5 | — | — | — |
| Aged DBR-silane 2 (Table 1) | — | 0.5 | — | — |
| Aged DBR-silane 3 (Table 1) | — | — | 0.5 | — |
| DBR-silane 4 (Table 1) | — | — | — | 0.5 |

The formulations were stirred in the dark for three days and then flow coated onto pre-cleaned Lexan® polycarbonate panels. The resulting coatings were air dried for one minute, dried at about 70° C. for four minutes, and then exposed to UV light by passing them five times under two 300 watt/inch medium pressure mercury lamps using a conveyor moving at about 25 ft/min. The initial haze of the resulting coatings as well as the haze of the coating solutions (in a 1 cm cell) are shown in Table 5. UVA 4 in composition D was essentially insoluble.

TABLE 5

Haze of coating solutions and cured coatings

| Formulation (Table 4) | % Haze of coating | % Haze of solution |
|---|---|---|
| A | 1.4 | 97.3 |
| B | 0.4 | 7.6 |
| C | 0.9 | 37.8 |
| D | 11.9 | — |

The coating prepared with Formulations A and D had unacceptable optical quality due to large amounts of insoluble material in the coating solution. Formulations prepared identically with A, B, and C using unaged UVA 1, 2, and 3 respectively gave essentially clear solutions and haze-free coatings.

What is claimed:

1. A silylated agent having the formula

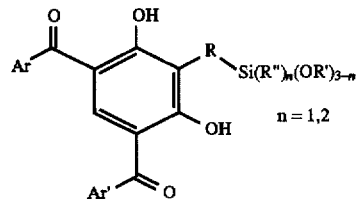

where Ar and Ar' are independently substituted or unsubstituted aromatic rings, R is a branched or unbranched chain of carbons, R' and R" are independently C1 to C12 alkyl or mixtures of C1 to C12 alkyl, and n is 1, 2, or 3.

2. A silylated agent in accordance with claim 1 where said agent is 4,6-dibenzoyl-2-(alkoxysilylalkyl) resorcinol.

3. A silylated agent in accordance with claim 1 where said agent is 4,6-dibenzoyl-2-(3-alkoxysilylpropyl) resorcinol.

4. A silicone hardcoat comprising:

a silylated agent having the formula

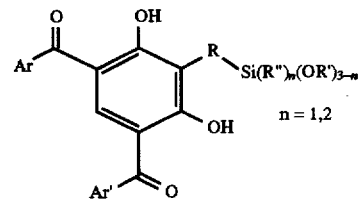

where Ar and Ar' are independently substituted or unsubstituted aromatic rings, R is a branched or unbranched chain of carbons, R' and R" are independently C1 to C12 alkyl or mixtures of C1 to C12 alkyl, and n is 1, 2, or 3; and a silicone compound containing composition.

5. A silicone hardcoat in accordance with claim 4 wherein said silicone compound containing composition has the formula $RSi(OR)_3$, where each R is independently an alkyl group having 1 to 3 carbon atoms or a substituted or unsubstituted aromatic radical.

6. A silicone hardcoat in accordance with claim 5 wherein each R is a methyl group.

7. A silicone hardcoat in accordance with claim 4 where said silylated agent is 4,6-dibenzoyl-2-(alkoxysilylalkyl) resorcinol.

8. A silicone hardcoat in accordance with claim 4 where said silylated agent is 4,6-dibenzoyl-2-(3-alkoxysilylpropyl) resorcinol.

9. A solid substrate with a silicone hardcoat applied thereon where said silicone hardcoat comprises:

a silylated agent having the formula

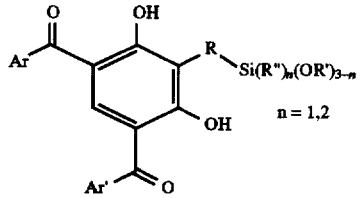

where Ar and Ar' are independently substituted or unsubstituted aromatic rings, R is a branched or unbranched chain of carbons, R' and R" are independently C1 to C12 alkyl or mixtures of C1 to C12 alkyl, and n is 1, 2, or 3; and a silicone compound containing composition.

10. A solid substrate in accordance with claim 9 where said silicone compound containing composition has the formula RSi(OR)$_3$, where each R is independently an alkyl group having 1 to 3 carbon atoms or a substituted or unsubstituted aromatic radical.

11. A solid substrate in accordance with claim 10 where each R is a methyl group.

12. A solid substrate in accordance with claim 9 where said silylated agent is 4,6-dibenzoyl-2-(alkoxysilylalkyl) resorcinol.

13. A solid substrate in accordance with claim 9 where said silylated agent is 4,6-dibenzoyl-2-(3-alkoxysilylpropyl) resorcinol.

14. A solid substrate in accordance with claim 9 where said solid substrate is a polycarbonate.

15. A solid substrate in accordance with claim 14 where said polycarbonate is a homopolycarbonate.

16. A solid substrate in accordance with claim 14 where said polycarbonate is a copolycarbonate.

17. A solid substrate in accordance with claim 14 where said polycarbonate is bisphenol A polycarbonate.

18. A solid substrate in accordance with claim 9 where said substrate is treated with a primer prior to applying said silicone hardcoat.

19. A UV curable acrylic coating comprising:

a compound useful for absorbing ultraviolet light having the formula

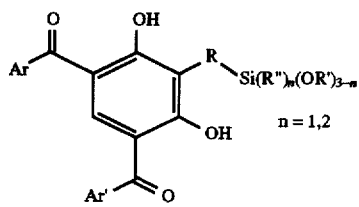

where Ar and Ar' are independently substituted or unsubstituted aromatic rings, R is a branched or unbranched chain of carbons, R' and R" are independently C1 to C12 alkyl or mixtures of C1 to C12 alkyl, and n is 1, 2, or 3; and a substantially transparent matrix composition.

20. A coating according to claim 19 where said transparent matrix is selected from the group consisting of acrylics, urethanes, melamines, and mixtures thereof.

21. A solid substrate with a UV curable acrylic coating composition applied thereon wherein said coating composition comprises:

a compound useful for absorbing ultraviolet light having the formula

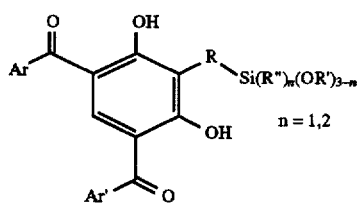

where Ar and Ar' are independently substituted or unsubstituted aromatic rings, R is a branched or unbranched chain of carbons, R' and R" are independently C1 to C12 alkyl or mixtures of C1 to C12 alkyl, and n is 1, 2, or 3; and a substantially transparent matrix composition.

* * * * *

UNITED STATES PATENT AND TRADEMARK OFFICE
CERTIFICATE OF CORRECTION

PATENT NO.     : 5,679,820
DATED          : October 21, 1997
INVENTOR(S)    : James Edward Pickett et al.

It is certified that error appears in the above-identified patent and that said Letters Patent is hereby corrected as shown below:

Title page,
Item [57], ABSTRACT, in formula II,
Line 7, cancel "n=1,2".
Line 11, cancel "n is 1 or 2" and substitute -- n is 1, 2, or 3 --.

Column 2,
Line 25, cancel "n=1,2".

Column 3,
Line 34, cancel "n=1".
Line 41, before "carbons" insert -- of --.

Column 4,
Line 24, in Table I, the 5th column, cancel "R" and substitute -- R" --.

Column 6,
Lines 25 and 45, cancel "n=1,2".
Lines 33 and 53, cancel "n is 1, 2, or 3" and substitute -- n is 1 or 2 --.

Column 7,
Line 11, cancel "n=1,2".
Line 19, cancel "n is 1, 2, or 3" and substitute -- n is 1 or 2 --.

Column 8,
Line 10, cancel "n=1,2".
Line 18, cancel "n is 1, 2, or 3" and substitute -- n is 1 or 2 --.

Signed and Sealed this

Twenty-third Day of September, 2003

JAMES E. ROGAN
*Director of the United States Patent and Trademark Office*